United States Patent
Vonk

[19]

[11] Patent Number: 5,913,880
[45] Date of Patent: Jun. 22, 1999

[54] PACEMAKER WITH AUTOMATIC SENSITIVITY ADJUSTMENT

[75] Inventor: Bernardus F. M. Vonk, Wehl, Netherlands

[73] Assignee: Vitatron Medical, B.V., Dieren, Netherlands

[21] Appl. No.: 08/835,349

[22] Filed: Apr. 7, 1997

[51] Int. Cl.⁶ .................................................. A61N 1/37
[52] U.S. Cl. ................................................. 607/27
[58] Field of Search .................................. 607/9, 27, 28, 607/5; 600/509, 517, 518, 521

[56] References Cited

U.S. PATENT DOCUMENTS

| | | |
|---|---|---|
| 4,708,144 | 11/1987 | Hamilton et al. . |
| 4,880,004 | 11/1989 | Baker, Jr. et al. . |
| 4,903,699 | 2/1990 | Baker, Jr. et al. . |
| 5,117,824 | 6/1992 | Keimel et al. . |
| 5,269,300 | 12/1993 | Kelly et al. ................................ 607/4 |
| 5,339,820 | 8/1994 | Henry et al. . |
| 5,476,485 | 12/1995 | Weinberg et al. ....................... 607/28 |
| 5,709,215 | 1/1998 | Perttu et al. ............................ 600/521 |
| 5,755,738 | 5/1998 | Kim et al. ................................. 607/9 |

*Primary Examiner*—Jeffrey R. Jastrzab
*Attorney, Agent, or Firm*—Woodcock Washburn Kurtz Mackiewicz & Norris, LLP

[57] ABSTRACT

There is provided a pacemaker having automatic adjustment of the sensitivity for sensing cardiac signals such as QRS, T and P waves. The pacemaker has software for examining each inputted signal, obtaining a measure of the peak amplitude, e.g. one-half, comparing such measure with a stored software sensitivity level, and adjusting the software sensitivity level each beat so that it effectively tracks beat-to-beat changes in the signal amplitude. The adjusted software sensitivity level is used for determining when an input signal is to be accepted as a true signal, or rejected.

20 Claims, 3 Drawing Sheets

PACEMAKER WITH AUTOMATIC SENSITIVITY ADJUSTMENT

FIELD OF THE INVENTION

This invention relates to pacemaker systems and, more particularly, systems and methods for adjusting the sensitivity level employed in sensing cardiac signals for use in controlling pacemaker operation.

BACKGROUND OF THE INVENTION

It is well known that it is very important to accurately set the sensitivity level, or threshold for receiving sensed signals, in an implantable pacemaker. Thus, in sensing cardiac signals, e.g., QRS, T, or P waves for use in controlling timing of pacemaker operations, it is important to be able to accept bonafide, or true signals, but block extraneous or noisy signals that may be detected at the lead electrodes. Many techniques have been developed for aiding in this task, as can be seen from the prior art. One technique is to filter the signals so as to enhance acceptance of only the type of waveform that is being monitored. Another technique is to use an adjustable "window" which allows the signal to be passed through the sense amplifier only around the time that the periodic signal is expected. But the most important technique is to set a threshold, or sensitivity level (also referred to herein as simply sensitivity), above which the input signal must rise before it is recognized. But a fixed sensitivity level is generally insufficient, since signal levels may change, rendering the fixed level inappropriate. Thus, if the level is too low, too much noise can pass through the sense circuitry; and if the level is too high, too many real signals can be lost because they don't pass the threshold, or sensitivity level.

There have been two primary approaches to solving the above sensitivity level problem. A first approach is to provide circuitry which sets the sensitivity based on observed peak values of the input signal. See, for example, U.S. Pat. No. 5,339,820. A second approach is to adjust the gain of the sense amplifier, i.e., increase the gain if the R wave peaks become lower, and decrease gain when such peaks become higher, to provide a substantially unchanging ratio of signal peak value to amplifier sensitivity. See, for example, U.S. Pat. Nos. 4,708,144; 4,880,004; and 4,903,699. However, these solutions do not provide for optimal adjustment of sensitivity on a beat-to-beat basis, i.e., they don't respond as quickly and accurately to changing conditions as desired. This is important in many situations, e.g., occurrences of ventricular tachycardia (VT) and ventricular fibrillation (VF); atrial fibrillation and atrial flutter.

SUMMARY OF THE INVENTION

It is an object of this invention to provide for automatic beat-by-beat adjustment of sensitivity in the sense channel of an implantable pacemaker or like device, so that sensitivity accurately tracks changes in input signal peak amplitude. It is a further object to provide such beat-by-beat capability in software form, so that sensitivity adjustment can be programmed from an external programmer.

In accordance with the above objects, there is provided, in a pacemaker embodiment, the capability of adjusting the sensitivity to input signals by automatically obtaining a measure of the peak amplitude of each input signal that is received periodically, comparing such measure with the last value of sensitivity, and adjusting the sensitivity up or down as a function of such comparison.

In a preferred embodiment, the automatic sensitivity adjustment is done by a software routine operated by a microprocessor in the pacemaker. Each time an input signal has a magnitude greater than a fixed minimal value, a trigger signal is generated which enables the software routine to analyze the signal amplitude and determine how the sensitivity should be adjusted. When the routine is thus enabled, the peak amplitude of the input signal is determined, and compared with a software sensitivity level maintained by the routine. A sensed signal is found, or indicated, only when the peak is greater than the software sensitivity level. The routine gets a fraction of the peak magnitude, e.g., one-half, and compares this fraction with the sensitivity level as adjusted during the prior cycle. If the fraction exceeds the sensitivity level, that level is incremented, preferably by a fixed amount, or delta value; if the fraction does not exceed the existing sensitivity level, the level is then decremented by the delta value. In any cycle where the peak amplitude does not exceed the software sensitivity level (and no sense is indicated to the pacemaker logic), the software sensitivity level is decremented by the delta value, with a lower limit corresponding to the fixed minimal value.

The preferred embodiment of the invention is the pacemaker environment. The scope of the invention extends to any type of pacemaker, implantable or external, and any operating mode. For example, the invention may be very useful for a VDD system which must process a broad range of variable signals, due to floating atrial rings. The invention also embraces external systems such as Pacing System Analyzers.

DESCRIPTION OF THE PREFERRED EMBODIMENTS

Figure 1:
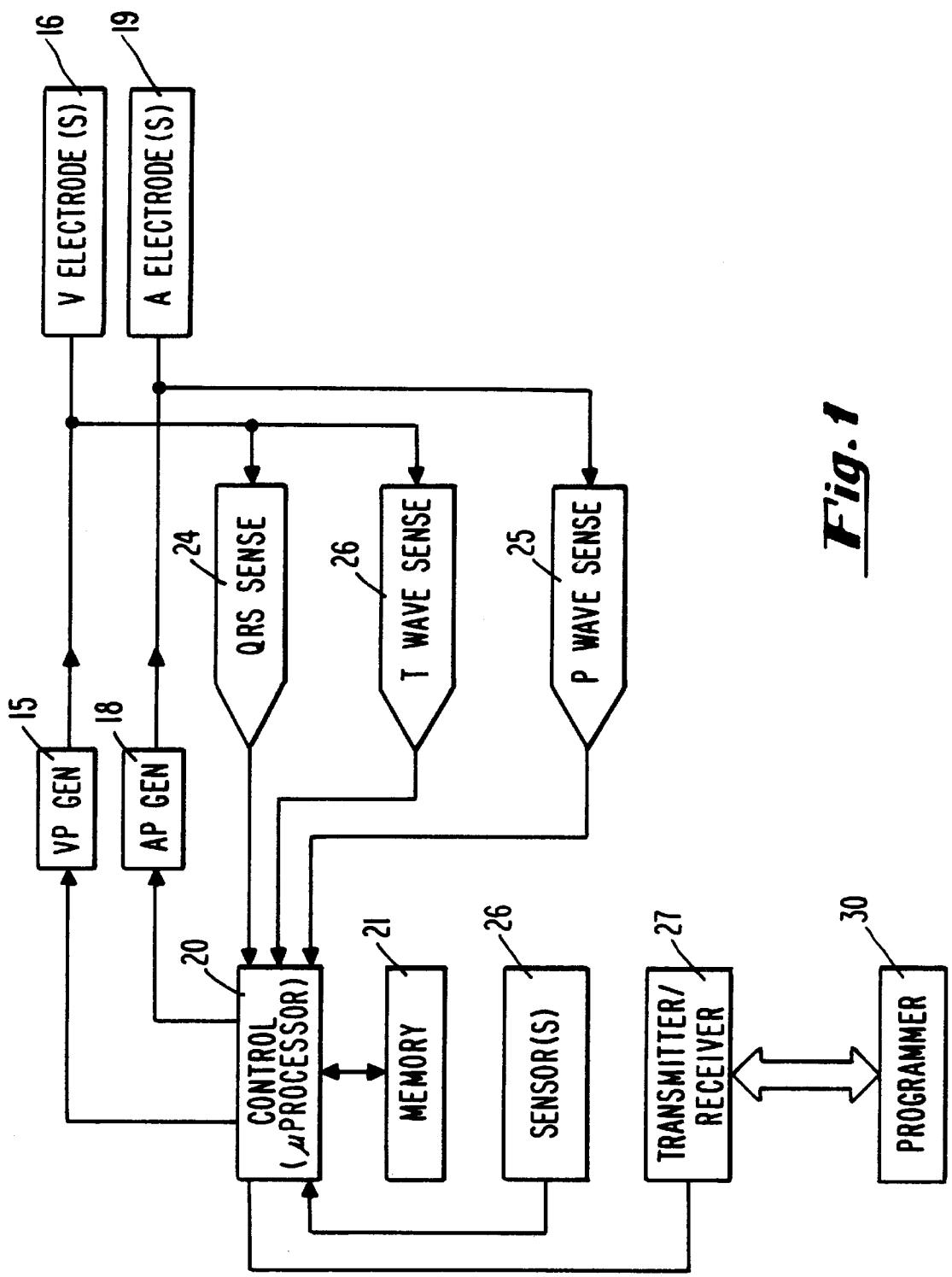
FIG. 1 is a block diagram of the primary components of a pacemaker in accord with this invention, indicating the respective sensing channels for sensing cardiac signals from the patient in which it is implanted.

Referring now to FIG. 1, there is shown a simplified block diagram of the primary components of a pacemaker as used in the system and method of this invention. Although a dual chamber pacemaker is illustrated for completeness, it is to be understood that the invention is equally applicable to single or dual chamber rate responsive pacemakers. A ventricular pace generator is illustrated at 15 for generating and delivering ventricular pace pulses under control of control unit 20, in a known fashion. The ventricular pace pulses are delivered to one or more ventricular electrodes illustrated at 16. Likewise an atrial pace generator is illustrated at 18, which generates atrial pace pulses under control block 20 and delivers the atrial pace pulses to one or more atrial electrodes as illustrated at 19. Sense signals from the ventricular electrode or electrodes are connected to QRS sense amplifier 24 and T-wave sense amplifier 26, the outputs of which are inputted to control block 20 for processing. Although not shown, it is understood that by those of skill in the pacemaker art that the input amplifiers 24, 26 are controlled in terms of timing by control unit 20. Likewise, signals detected in the atrium by electrodes 19 are delivered to P-wave sense amplifier 25, the output of which is connected through to control 20.

Control block 20 suitably incorporates a microprocessor with associated software, the software being stored in memory 21, as indicated. Memory 21 may contain RAM and ROM, and the assignment of pacemaker functions can be divided between hardware and software in any desired manner. In the preferred embodiment of this invention, the algorithms are suitably carried out under software control. One or more sensors 26 may be provided to continuously detect rate-indicating parameters, the parameter signals being inputted to control block 24 to provide rate responsive control, in a known manner. As illustrated at 27, the pacemaker suitably has a transmitter/receiver for receiving programmer communications from an external programmer, and for transmitting collected data back to a transmitter, in a known fashion.

Figure 2:
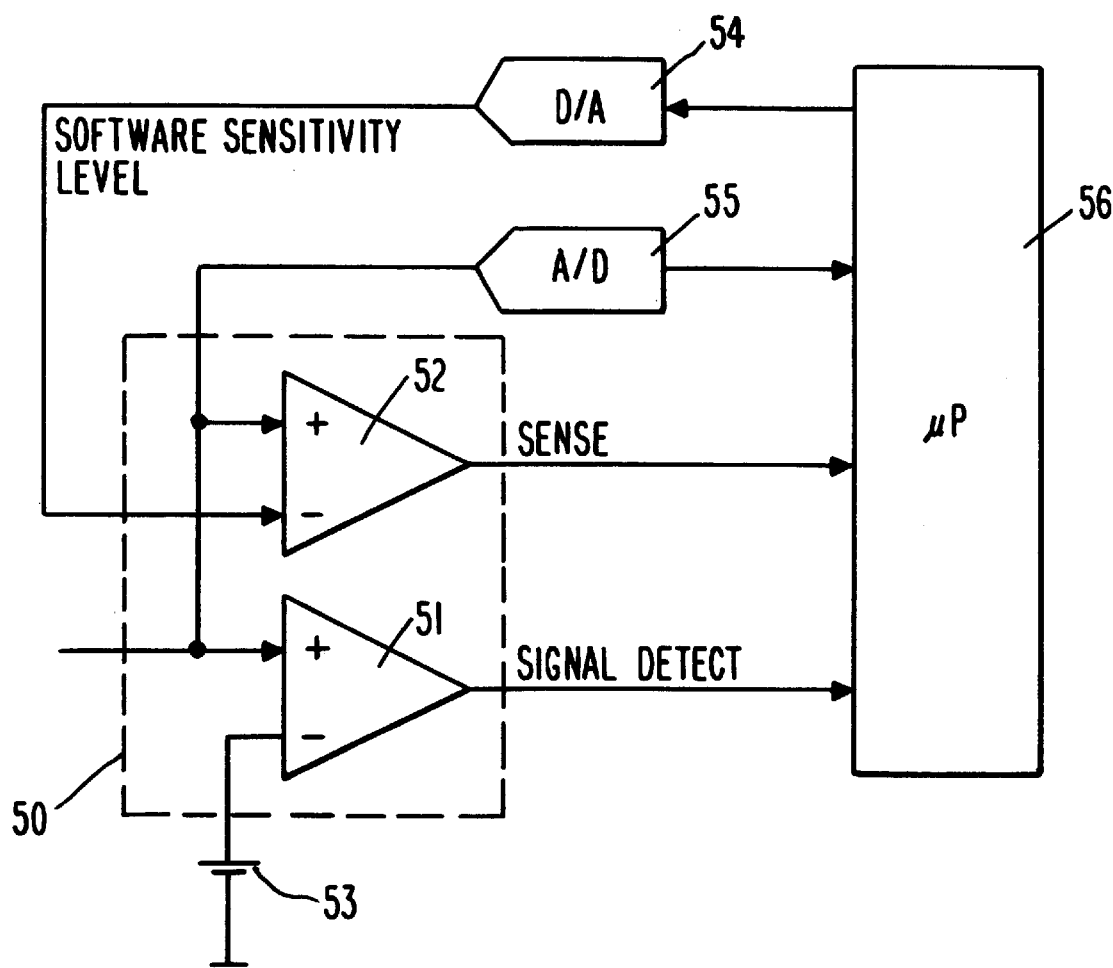
FIG. 2 is a block diagram of a hardware embodiment of the automatic sensitivity adjustment feature of this invention.

Referring now to FIG. 2, there is shown a block diagram of the primary components of a combined hardware and software embodiment of this invention, indicating the functions carried out by software under control of microprocessor 56. The input signal, e.g., the QRS or P wave, is derived from the ventricular or atrial electrodes and inputted to sense amplifier circuitry 50, which may be circuit 24, 25 or 26 as illustrated in FIG. 1. Specifically, the signal is inputted to one of the two input terminals of signal detect amplifier 51. The other input terminal of amplifier 51 is connected to a fixed voltage source, indicated at 53, which is nominally a 0.25 millivolt supply. Amplifier 51 is a differential amplifier which provides an output only when the input signal exceeds the fixed value of 0.25 mV. Suitably, the input signal is first inverted so that if it is a negative-going signal as sent to the pacemaker, it is compared to the plus 0.25 mV reference. Whenever the absolute value of the input exceeds the 0.25 mV reference, a trigger signal is sent to microprocessor 56, telling it that a signal has been received having a peak absolute amplitude of at least 0.25 mV. The input signal is also connected to a first input of sense amplifier 52, and to A/D converter 55. The input to amplifier 52 is compared to a stored value of a software sensitivity level, which is D/A converted through converter 54 and inputted to the other terminal of amplifier 52. Whenever the input peak amplitude exceeds the software sensitivity level, a sense signal is generated and inputted to the microprocessor 56, for use in pacemaker control in a well known manner. Also, when a trigger signal is received by microprocessor 56, it generates an enable signal which is connected to converter 55, enabling it to sample the input signal at its peak and to deliver digital signals to the microprocessor. Microprocessor 56 carries out the functions of determining the peak value of the sampled signal; getting a fraction of such peak value, e.g. one-half; comparing the fraction with the stored value of the software sensitivity level; and adjusting the software sensitivity level and storing the new adjusted value. For example, if the one-half peak value is less than the stored value, the value is decremented and the new value stored; if greater, then the value is incremented, and the new value stored. In this manner, the software sensitivity level is adjusted each cycle, so that it effectively tracks changes in the amplitude of the received signal.

Figure 3:
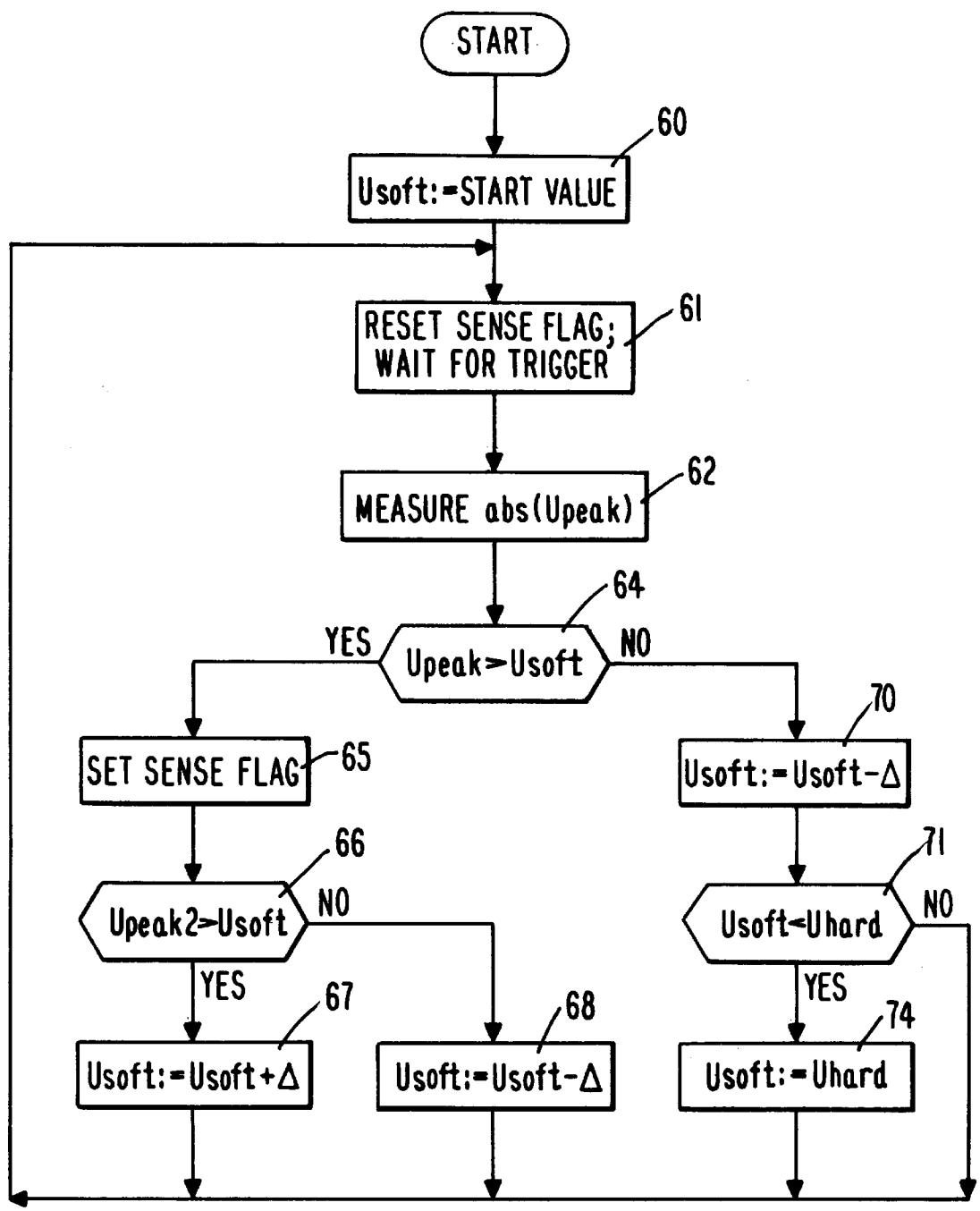
FIG. 3 is a flow diagram of a software embodiment of the automatic sensitivity adjustment feature of this invention.

Referring now to FIG. 3, there is shown a software routine, stored in memory and run by microprocessor 56, for carrying out the beat-by-beat sensitivity adjustment in accordance with this invention. After the routine is started, a start value of Usoft, the software sensitivity level, is set to a start value as seen at block 60, the start value suitably being programmed through programmer 30. Then, at 61, the sense flag is reset, and the routine waits for a trigger from amplifier 51. When a trigger is received, the absolute peak value of the input signal is determined at 62. Then, at 64, the routine compares Upeak to Usoft. If Upeak is greater than Usoft, the routine branches to block 65, and sets the sense flag, thus signaling to the pacemaker logic that a valid signal has been sensed. At 66, the variable Upeak/2 is obtained and compared with Usoft. If Upeak/2 is greater, then at 67 Usoft is set to Usoft plus delta and stored, where delta is suitably a programmable constant. If the comparison at 66 indicates that Upeak/2 is not greater than Usoft, then at 68, Usoft is set to Usoft minus delta, and stored. In this manner, Usoft is constantly adjusted around the changing value of Upeak/2. Of course, another fraction could be chosen, one-half peak value being exemplary.

Returning to block 64, if Upeak is not greater than Usoft, then at block 70 Usoft is set equal to Usoft minus delta. At 71, the routine checks to see whether this has made Usoft less than Uhard, the trigger level (e.g., 0.25 mV), and if yes at 74 set Usoft equal to Uhard.

There have thus been shown two embodiments incorporating software for automatically calculating a new effective sensitivity each cycle, continually adjusting, the sensitivity with respect to the peak amplitude of the signal being sensed. In a pacemaker as illustrated in FIG. 1, this feature can be incorporated for each signal. i.e., for any one or all three of the R, T and P-waves. The variables can be programmed, e.g., the measure of the peak amplitude for comparison can be programmed to be 0.5, 0.6, or any fraction; and the delta values can be re-programmed.

What is claimed is:

1. An implantable cardiac pacemaker for pacing a patient as a function of sensed cardiac signals from said patient's heart, comprising:

stimulus means for delivering stimulus pulses to said patient's heart;

sensing means for sensing said patient cardiac signals, said sensing means having measure means for determining a measure of the magnitude of sensed signals, comparing means for comparing each said determined measure to a variable reference and for recognizing a sense when said measure is greater than said reference, and means for adjusting said reference as a function of said comparing; and control means for controlling said stimulus means as a function of said recognized senses.

2. The pacemaker as described in claim 1, comprising signal means for determining each occurrence when a said sensed signal has a magnitude at least as great as a first level and enabling means for enabling said measure means in response to each said occurrence.

3. The pacemaker as described in claim 2, wherein said adjusting means comprises peak means for determining a peak value of each cardiac signal and fraction means for generating said measure as a fraction of said peak value.

4. The pacemaker as described in claim 3, comprising a software routine for providing said adjusting means.

5. A system in an implantable pacemaker for sensing patient cardiac signals and automatically adjusting the sensitivity level for accepting a signal as a true cardiac signal, comprising:

sense means for sensing said cardiac signals having a peak magnitude above a predetermined level; measure means for obtaining a measure of the peak value of each said sensed signal;

sensitivity means for providing a variable sensitivity level, said sensitivity means having a software routine for adjusting said variable sensitivity level as a function of each said sensed software means having means for comparing said peak value measure with said sensitivity level, and adjusting means for adjusting said sensitivity level as a function of said comparison signal.

6. The system as described in claim 5, wherein said measure means has means for measuring an absolute peak value of each said sensed signal.

7. The system as described in claim 5, wherein said software routine has fraction means for obtaining a fraction of said peak value, and second comparing means for comparing said fraction with said variable sensitivity level, and wherein said adjusting means has means for adjusting said variable sensitivity level as a function of the comparison of said fraction with said variable sensitivity level.

8. The system as described in claim 7, wherein said fraction means has means for obtaining one-half of said peak value.

9. The system as described in claim 5, wherein said software routine has limit means for limiting said sensitivity level to a lower limit of said predetermined level.

10. A method of automatically setting the sense sensitivity level of a pacemaker to a level related to the peak amplitude of periodic input signals being sensed, comprising:

comparing each said input signal to a predetermined minimum reference level and providing a trigger signal each time said input signal is greater than said reference level;

converting said input signal to a digital signal in response to a said trigger signal and determining the peak value of said digital signal;

maintaining by software a software sensitivity level;

comparing each said peak value with said sensitivity level, and indicating a sensed signal only when said peak value exceeds said sensitivity level; and said maintaining including adjusting said sensitivity level following each said trigger signal so that said sensitivity level is varied as a function of said peak value and the prior maintained sensitivity level.

11. The method as described in claim 10, comprising carrying out said maintaining and comparing steps by a software routine.

12. The method as described in claim 11, wherein said adjusting comprises determining a predetermined fraction of said peak value, determining whether said fraction is greater or less than the value of said sensitivity level, and adjusting said sensitivity level as a function of said determining.

13. The method as described in claim 12, comprising setting said predetermined fraction to about one half.

14. The method as described in claim 12, wherein said adjusting step comprises adjusting said sensitivity level by a predetermined amount.

15. The method as described in claim 14, wherein said adjusting comprises incrementing said software sensitivity level by said amount when said fraction is greater than said software sensitivity level.

16. The method as described in claim 14, wherein said adjusting comprises decrementing said software sensitivity level by said amount when said fraction is lesser than said software sensitivity level.

17. The method as described in claim 15, comprising programming said fraction and said amount from an external programmer.

18. The method as described in claim 10, wherein said adjusting comprises decrementing said software sensitivity level when said comparing indicates that said peak value does not exceed said software sensitivity level.

19. The method as described in claim 10, comprising detecting depolarization signals from a patient's ventricle, and providing said depolarization signals as said input signals.

20. The method as described in claim 10, comprising detecting depolarization signals from a patient's atrium, and providing said depolarization signals as said input signals.

* * * * *